United States Patent
Murata et al.

(10) Patent No.: US 10,918,578 B2
(45) Date of Patent: Feb. 16, 2021

(54) DENTAL CURABLE COMPOSITION

(71) Applicant: GC Corporation, Shizuoka (JP)

(72) Inventors: Takayuki Murata, Tokyo (JP); Takumasa Kimura, Tokyo (JP); Yui Tei, Tokyo (JP); Azusa Miyagawa, Tokyo (JP)

(73) Assignee: GC Corporation, Shizuoka (JP)

( * ) Notice: Subject to any disclaimer, the term of this patent is extended or adjusted under 35 U.S.C. 154(b) by 0 days.

(21) Appl. No.: 16/488,673

(22) PCT Filed: Dec. 6, 2017

(86) PCT No.: PCT/JP2017/043871
§ 371 (c)(1),
(2) Date: Aug. 26, 2019

(87) PCT Pub. No.: WO2018/154911
PCT Pub. Date: Aug. 30, 2018

(65) Prior Publication Data
US 2019/0380918 A1 Dec. 19, 2019

(30) Foreign Application Priority Data
Feb. 27, 2017 (JP) .............................. JP2017-035297

(51) Int. Cl.
A61K 6/887 (2020.01)
A61K 6/16 (2020.01)
A61K 6/17 (2020.01)
A61K 6/836 (2020.01)
C08L 33/12 (2006.01)
C08L 43/04 (2006.01)

(52) U.S. Cl.
CPC .............. A61K 6/887 (2020.01); A61K 6/16 (2020.01); A61K 6/17 (2020.01); A61K 6/836 (2020.01); C08L 33/12 (2013.01); C08L 43/04 (2013.01)

(58) Field of Classification Search
None
See application file for complete search history.

(56) References Cited

U.S. PATENT DOCUMENTS

| 3,442,851 | A | * | 5/1969 | McManimie | C08F 220/12 524/492 |
| 5,192,815 | A | * | 3/1993 | Okada | C07F 7/10 523/115 |
| 5,354,785 | A | * | 10/1994 | Rheinberger | A61K 6/887 523/116 |
| 6,306,927 | B1 | * | 10/2001 | Blackwell | A61K 6/887 523/116 |
| 6,500,004 | B2 | * | 12/2002 | Jensen | A61K 6/887 433/228.1 |
| 6,593,395 | B2 | * | 7/2003 | Angeletakis | A61K 6/71 523/115 |
| 6,812,266 | B2 | * | 11/2004 | Klee | A61K 6/30 522/171 |
| 6,890,968 | B2 | * | 5/2005 | Angeletakis | A61K 6/76 523/115 |
| 6,899,948 | B2 | * | 5/2005 | Zhang | A61K 6/891 428/331 |
| 7,001,932 | B2 | * | 2/2006 | Blackwell | A61K 6/887 523/116 |
| 7,275,932 | B2 | * | 10/2007 | Jin | A61K 6/54 433/228.1 |
| 7,393,882 | B2 | * | 7/2008 | Wu | A61K 6/891 523/116 |
| 7,780,449 | B2 | * | 8/2010 | Fischer | A61K 6/54 433/224 |

(Continued)

FOREIGN PATENT DOCUMENTS

| EP | 3272325 | 1/2018 |
| JP | H02-134307 | 5/1990 |
| JP | 2017-014111 | 1/2017 |
| WO | 02/05752 | 1/2002 |
| WO | 2008/093596 | 8/2008 |
| WO | 2014/050634 | 4/2014 |
| WO | 2016/152659 | 9/2016 |

OTHER PUBLICATIONS

International Search Report for PCT/JP2017/043871 dated Jan. 16, 2018.

Primary Examiner — Peter A Salamon
(74) Attorney, Agent, or Firm — IPUSA, PLLC

(57) ABSTRACT

According to one aspect of the present invention, a dental curable composition includes: polymerizable monomers; inorganic particles (A1) and/or inorganic particles (A2) (excluding the inorganic particles (A2); and inorganic particles (B). The inorganic particles (A1) are surface-treated with a compound expressed by a general formula (1) and have a volume-median particle size of greater than or equal to 0.1 µm and less than or equal to 0.9 µm. The inorganic particles (A2) are surface-treated with a compound expressed by a general formula (2) and have a volume-median particle size of greater than or equal to 0.1 µm and less than or equal to 0.9 µm. The inorganic particles (B) are particles where a group expressed by a general formula (A) is present at surfaces, are particles where a group expressed by a general formula (B) is present at surfaces, and/or are particles surface-treated with a compound expressed by a general formula (3) and have an average primary particle size of greater than or equal to 5 nm and less than or equal to 50 nm. A ratio of a mass of the inorganic particles (B) to a total mass of the inorganic particles (A1), the inorganic particles (A2), and the inorganic particles (B) is greater than or equal to 0.001 and less than or equal to 0.015.

3 Claims, No Drawings

(56) References Cited

U.S. PATENT DOCUMENTS

| | | | |
|---|---|---|---|
| 7,828,550 B2 * | 11/2010 | Wagner | A61C 5/50 433/224 |
| 7,951,851 B2 * | 5/2011 | Kuboe | A61K 6/17 523/116 |
| 8,278,368 B2 * | 10/2012 | Rusin | A61K 6/20 523/116 |
| 8,436,078 B2 * | 5/2013 | Okubayashi | A61K 6/887 523/216 |
| 8,440,739 B2 * | 5/2013 | Okubayashi | A61K 6/887 523/115 |
| 8,455,564 B2 * | 6/2013 | Kuboe | A61K 6/76 523/115 |
| 8,552,087 B2 * | 10/2013 | Zappini | A61K 6/58 523/116 |
| 8,710,114 B2 * | 4/2014 | Rusin | A61K 6/71 523/116 |
| 8,790,707 B2 * | 7/2014 | Rusin | A61K 8/11 424/490 |
| 8,957,126 B2 * | 2/2015 | Rusin | C03C 3/19 523/115 |
| 9,109,072 B2 * | 8/2015 | Takahashi | C08F 2/44 |
| 9,119,774 B2 * | 9/2015 | Gross | A61K 6/893 |
| 9,724,275 B2 * | 8/2017 | Schuhmacher | A61K 6/887 |
| 10,137,061 B2 * | 11/2018 | Rusin | A61K 6/891 |
| 10,441,512 B2 * | 10/2019 | Tanaka | C08K 9/06 |
| 2003/0162863 A1 * | 8/2003 | Satoh | A61K 6/887 523/109 |
| 2010/0105802 A1 * | 4/2010 | Kuboe | A61K 6/17 523/116 |
| 2013/0172441 A1 | 7/2013 | Takahata et al. | |
| 2014/0378571 A1 * | 12/2014 | Takahashi | C08F 2/44 522/33 |
| 2015/0272833 A1 | 10/2015 | Toriyabe et al. | |
| 2019/0380918 A1 * | 12/2019 | Murata | A61K 6/884 |

* cited by examiner

DENTAL CURABLE COMPOSITION

TECHNICAL FIELD

The present invention relates to a dental curable composition.

BACKGROUND ART

Flowable composite resins generally include polymerizable monomers and inorganic fillers, and are widely used as materials for filling and repairing lost portions of teeth or dental caries.

Conventionally, flowable composite resins that can satisfy polishability, abrasion resistance formability, handleability and flexural strength are desired.

Patent Document 1 describes a dental curable composition including: a polymerizable monomer, inorganic particles (A), and inorganic particles (B). Here, the inorganic particles (A) are surface-treated with a compound expressed by a general formula (1) and have a volume-median particle size of greater than or equal to 0.1 μm and less than or equal to 0.9 μm. Also, for the inorganic particles (B), a group expressed by a general formula (A) and/or a group expressed by a general formula (B) is present at surfaces, and the average primary particle size is greater than or equal to 5 nm and less than or equal to 50 nm. Further, a ratio of a mass of the inorganic particles (B) to a total mass of the inorganic particles (A) and the inorganic particles (B) is greater than or equal to 0.02 and less than or equal to 0.05.

PRIOR ART DOCUMENTS

Patent Documents

[Patent Document 1] International Publication Pamphlet No. WO 2016/152659

DISCLOSURE OF THE INVENTION

Problem to be Solved by the Invention

However, it is desired to reduce stringiness of a flowable composite resin and to suppress liquid separation.

When the stringiness of a flowable composite resin is large, the flowable composite resin that is stringy and adheres to a peripheral portion of a cavity causes adhesion failure.

In view of the problems of the conventional art as described above, one aspect of the present invention has an object to provide a flowable composite resin that has reduced stringiness, suppresses liquid separation, and is able to satisfy polishability, abrasion resistance formability, handleability and flexural strength.

According to one aspect of the present invention, a dental curable composition includes: polymerizable monomers; inorganic particles (A1) and/or inorganic particles (A2) (excluding the inorganic particles (A2); and inorganic particles (B).

The inorganic particles (A1) are surface-treated with a compound expressed by a general formula $$CH_2{=}C{-}\overset{O}{\overset{\|}{C}}{-}O{-}(CH_2)_q{-}\underset{R^2_p}{\overset{|}{Si}}{-}R^3_{(3-p)} \quad (1)$$
$$\phantom{CH_2{=}}\underset{R^1}{|}$$

(in the formula, $R^1$ is a hydrogen atom or a methyl group, $R^2$ is a hydrolyzable group, $R^3$ is a hydrocarbon group having 1 to 6 carbon atoms, p is 2 or 3, and q is an integer greater than or equal to 6 and less than or equal to 13), and the inorganic particles (A1) have a volume-median particle size of greater than or equal to 0.1 μm and less than or equal to 0.9 μm.

The inorganic particles (A2) are surface-treated with a compound expressed by a general formula $$CH_2{=}C{-}\overset{O}{\overset{\|}{C}}{-}O{-}(CH_2)_q{-}\underset{R^2_p}{\overset{|}{Si}}{-}R^3_{(3-p)} \quad (2)$$
$$\phantom{CH_2{=}}\underset{R^1}{|}$$

(in the formula, $R^1$ is a hydrogen atom or a methyl group, $R^2$ is a hydrolyzable group, $R^3$ is a hydrocarbon group having 1 to 6 carbon atoms, p is 2 or 3, and q is an integer greater than or equal to 1 and less than or equal to 5), and the inorganic particles (A2) have a volume-median particle size of greater than or equal to 0.1 μm and less than or equal to 0.9 μm.

The inorganic particles (B) are particles where a group expressed by a general formula $$\begin{array}{c}{-}O\\{\phantom{-}}\phantom{O}\diagdown\\{\phantom{-O}}Si\\{\phantom{-}}\phantom{O}\diagup\phantom{\diagdown}\diagdown\\{-}O\phantom{\diagup}\phantom{Si}R^5\end{array}\phantom{xxx}R^4 \quad (A)$$

(in the formula, $R^4$ and $R^5$ are independently a methyl group or an ethyl group) is present at surfaces, are particles where a group expressed by a general formula $$-O-\underset{R^8}{\overset{R^6}{\overset{|}{Si}}}-R^7 \quad (B)$$

(in the formula $R^6$, $R^7$, and $R^8$ are independently a methyl group or an ethyl group) is present at surfaces, and/or are particles surface-treated with a compound expressed by a general formula $$CH_2{=}C{-}\overset{O}{\overset{\|}{C}}{-}O{-}(CH_2)_q{-}\underset{R^2_p}{\overset{|}{Si}}{-}R^3_{(3-p)} \quad (3)$$
$$\phantom{CH_2{=}}\underset{R^1}{|}$$

(in the formula $R^1$ is a hydrogen atom or a methyl group, $R^2$ is a hydrolyzable group, $R^3$ is a hydrocarbon group having 1 to 6 carbon atoms, p is 2 or 3, and q is an integer greater than or equal to 1 and less than or equal to 6), and the inorganic particles (B) have an average primary particle size of greater than or equal to 5 nm and less than or equal to 50 nm. A ratio of a mass of the inorganic particles (B) to a total mass of the inorganic particles (A1), the inorganic particles (A2), and the inorganic particles (B) is greater than or equal to 0.001 and less than or equal to 0.015.

Effects of the Invention

According to one aspect of the present invention, it is possible to provide a flowable composite resin that has reduced stringiness, suppresses liquid separation, and is able to satisfy polishability, abrasion resistance formability, handleability and flexural strength.

EMBODIMENT FOR CARRYING OUT THE INVENTION

Next, an embodiment of the present invention will be described.

A dental curable composition of the present embodiment includes polymerizable monomers; inorganic particles (A1) and/or inorganic particles (A2) (excluding inorganic particles (A2)); and inorganic particles (B).

The inorganic particles (A1) are surface-treated with a compound expressed by a general formula (1). Therefore, it is possible to achieve the flexural strength, the abrasion resistance, and the polishability of a flowable composite resin.

The volume-median particle size of the inorganic particles (A1) is 0.1 µm to 0.9 µm, and is preferably 0.15 µm to 0.70 µm. When the volume-median particle size of the inorganic particles (A1) is less than 0.1 µm, the flexural strength of a flowable composite resin decreases. When the volume-median particle size of the inorganic particles (A1) exceeds 0.9 µm, the flexural strength, the abrasion resistance, and the polishability of a flowable composite resin decrease.

The inorganic particles (A2) are surface-treated with a compound expressed by a general formula (2). Therefore, it is possible to enhance achieve the formability and the handleability of a flowable composite resin.

The volume-median particle size of the inorganic particles (A2) is 0.1 µm to 0.9 µm, and is preferably 0.15 µm to 0.70 µm. When the volume-median particle size of the inorganic particles (A2) is greater than or equal to 0.1 µm, the flexural strength of a flowable composite resin can be enhanced. When the volume-median particle size of the inorganic particles (A2) is less than or equal to 0.9 µm, the flexural strength, the abrasion resistance, and the polishability of a flowable composite resin can be enhanced.

Note that the volume-median particle sizes of the inorganic particles (A1) and the inorganic particles (A2) can be measured by laser diffraction scattering.

The inorganic particles (B) are particles where a group expressed by a general formula (A) is present at surfaces, are particles where a group expressed by a general formula (B) is present at surfaces, and/or are particles surface-treated with a compound expressed by a general formula (3). Thus, liquid separation of a flowable composite resin can be suppressed.

The average primary particle size of the inorganic particles (B) is 5 nm to 50 nm, and is preferably 5 nm to 20 nm. When the average primary particle size of the inorganic particles (B) is less than 5 nm, manufacturing becomes difficult. When the average primary particle size of the inorganic particles (B) exceeds 50 nm, liquid separation of a flowable composite resin easily occurs.

Note that the average primary particle size of the inorganic particles (B) is the average value of the primary particle sizes of 100 inorganic particles (B) randomly selected after taking an electron micrograph.

The ratio of the mass of the inorganic particles (B) to a total mass of the inorganic particles (A1), the inorganic particles (A2), and the inorganic particles (B) is between 0.001 and 0.015, and is preferably between 0.001 and 0.010. When the ratio of the mass of the inorganic particles (B) to the total mass of the inorganic particles (A1), the inorganic particles (A2), and the inorganic particles (B) is less than 0.001, liquid separation of a flowable composite resin easily occurs. When the ratio of the mass of the inorganic particles (B) to the total mass of the inorganic particles (A1), the inorganic particles (A2), and the inorganic particles (B) exceeds 0.015, the stringiness of a flowable composite resin increases.

It is preferable that the ratio of the mass of the inorganic particles (A1) to the total mass of the inorganic particles (A1), the inorganic particles (A2), and the inorganic particles (B) is greater than or equal to 0.2. This makes it possible to enhance the formability and handleability of a flowable composite resin.

Next, the polymerizable monomers, the inorganic particles (A1), the inorganic particles (A2), and the inorganic particles (B) will be described.

The refractive index of a polymer of the polymerizable monomers is normally 1.52 to 1.58, and is preferably 1.53 to 1.58.

Note that the refractive index means a refractive index measured using an Abbe refractometer at 25° C.

The polymerizable monomers are preferably radical polymerizable monomers.

The polymerizable monomers are not limited in particular and may be esters of α-cyanoacrylic acid, (meth)acrylic acid, α-haloacrylic acid, crotonic acid, cinnamic acid, sorbic acid, maleic acid, itaconic acid, etc., (meth)acrylamide, (meth)acrylamide derivatives, vinyl esters, vinyl ethers, mono-N-vinyl derivatives, styrene derivatives, or the like, and two or more kinds of these may be used in combination as the polymerizable monomers. Among these, (meth) acrylic esters and (meth)acrylamide derivatives are preferable, and (meth)acrylic esters are more preferable.

Examples of monofunctional (meth)acrylic esters and (meth)acrylamide derivatives include methyl (meth)acrylate, isobutyl (meth)acrylate, benzyl (meth)acrylate, lauryl (meth)acrylate, 2,3-dibromopropyl (meth)acrylate, 2-hydroxyethyl (meth)acrylate, 6-hydroxyhexyl (meth)acrylate, 10-hydroxydecyl (meth)acrylate, propylene glycol mono (meth)acrylate, glycerin mono(meth)acrylate, erythritol mono(meth)acrylate, N-methylol(meth)acrylamide, N-hydroxyethyl(meth)acrylamide, N-(dihydroxyethyl)(meth) acrylamide, (meth)acryloyloxydodecylpyridinium bromide, (meth)acryloyloxydodecylpyridinium chloride, (meth)acryloyloxyhexadecylpyridinium chloride, (meth)acryloyloxydecylammonium chloride, and the like.

Examples of difunctional (meth)acrylic esters include ethylene glycol di(meth)acrylate, triethylene glycol di(meth) acrylate, propylene glycol di(meth)acrylate, neopentyl glycol di(meth)acrylate, 1,6-hexanediol di(meth)acrylate, 1,10-decanediol di(meth)acrylate, 2,2-bis[4-[3-(meth) acryloyloxy-2-hydroxypropoxy]phenyl]propane, 2,2-bis[4-(2-(meth)acryloyloxyethoxy)phenyl]propane, 2,2-bis[4-(meth)acryloyloxypolyethoxyphenyl]propane, 1,2-bis[3-(meth)acryloyloxy-2-hydroxypropoxy]ethane, pentaerythritol di(meth)acrylate, [2,2,4-trimethylhexamethylene bis(2-carbamoyloxyethyl)]di(meth)acrylate, and the like.

Examples of tri- or higher-functional (meth)acrylic esters include trimethylolpropane tri(meth)acrylate, trimethylolethane tri(meth)acrylate, tetramethylolmethane tri(meth)

acrylate, pentaerythritol tetra(meth)acrylate, dipentaerythritol hexa(meth)acrylate, N,N'-(2,2,4-trimethylhexamethylene)bis[2-(aminocarboxy)propane-1,3-diol]tetramethacrylate, 1,7-diacryloyloxy-2,2,6,6-tetraacryloyloxymethyl-4-oxyheptane, and the like.

The ratio of the mass of the polymerizable monomers to the total mass of the inorganic particles (A1), the inorganic particles (A2), and the inorganic particles (B) is normally between 0.1 and 1.5, and is preferably between 0.25 and 0.65.

The inorganic particles (A) may be spherical, but are preferably irregularly shaped. Because this increases the specific surface area of the inorganic particles (A1), it is possible to increase the bondability with the polymerizable monomers, thus making it possible to enhance the flexural strength.

$R^2$ in the general formula (1) is not limited in particular, and may be an alkoxy group such as a methoxy group, an ethoxy group, and a butoxy group, a chlorine atom, an isocyanate group, or the like.

$R^3$ in the general formula (1) is not limited in particular, and may be an alkyl group having 1 to 6 carbon atoms, an alkenyl group having 2 to 6 carbon atoms, an alkynyl groups having 2 to 6 carbon atoms, or the like.

An alkyl group having 1 to 6 carbon atoms may be linear, branched, or cyclic, and may be, for example, a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, an n-hexyl group, a cyclopropyl group, a cyclobutyl group, a cyclopentyl group, a cyclohexyl group, or the like.

An alkenyl group having 2 to 6 carbon atoms may be linear, branched, or cyclic, and may be, for example, a vinyl group, an allyl group, a methylvinyl group, a butenyl group, a pentenyl group, a hexenyl group, a cyclopropenyl group, a cyclobutenyl group, a cyclopentenyl group, a cyclohexenyl group, or the like.

An alkynyl group having 2 to 6 carbon atoms may be linear, branched, or cyclic, and may be, for example, an ethynyl group, a 1-propynyl group, a 2-propynyl group, a 1-butynyl group, a 1-methyl-2-propynyl group, a 2-butynyl group, a 3-butynyl group, a 1-pentynyl group, a 1-ethyl-2-propynyl group, a 2-pentynyl group, a 3-pentynyl group, a 1-methyl-2-butynyl group, a 4-pentynyl group, a 1-methyl-3-butynyl group, a 2-methyl-3-butynyl group, a 1-hexynyl group, a 2-hexynyl group, a 1-ethyl-2-butynyl group, a 3-hexynyl group, a 1-methyl-2-pentynyl group, a 1-methyl-3-pentynyl group, a 4-methyl-1-pentynyl group, a 3-methyl-1-pentynyl group, a 5-hexynyl group, a 1-ethyl-3-butynyl group, or the like.

Here, q in the general formula (1) is an integer greater than or equal to 6 and less than or equal to 13, and is preferably an integer greater than or equal to 8 and less than or equal to 13.

The compound expressed by the general formula (1) is not limited in particular, and may be 6-methacryloyloxyhexyltrimethoxysilane, 7-methacryloyloxyheptyltrimethoxysilane, 8-methacryloyloxyoctyltrimethoxysilane, 8-acryloyloxyoctyltrimethoxysilane, 8-methacryloyloxyoctyltriethoxysilane, 9-methacryloyloxynonyltrimethoxysilane, 10-methacryloyloxydecyltrimethoxysilane, 11-methacryloyloxyundecyltrimethoxysilane, 11-methacryloyloxyundecyldichloromethylsilane, 11-methacryloyloxyundecyltrichlorosilane, 11-methacryloyloxyundecyldimethoxymethylsilane, 12-methacryloyloxydodecyltrimethoxysilane, 13-methacryloyloxytridecyltrimethoxysilane, or the like, and two or more kinds of these may be used in combination as the compound expressed by the general formula (1). Among these, 8-methacryloyloxyoctyltrimethoxysilane, 9-methacryloyloxynonyltrimethoxysilane, 10-methacryloyloxydecyltrimethoxysilane, and 11-methacryloyloxyundecyltrimethoxysilane are preferable.

A method of surface-treating the inorganic particles (A1) is not limited in particular, and may be a method by which the inorganic particles (A1) before being surface-treated are sprayed with a solution obtained, by diluting the compound expressed by the general formula (1) diluted with a solvent, while being stirred in a mixing tank and are heated and dried for a certain time in the tank while being kept stirred, a method by which the inorganic particles (A1) before being surface-treated and a compound expressed by the general formula (1) are stirred and mixed in a solvent and are thereafter heated to be dried, or the like.

The mass ratio of the compound expressed by the general formula (1) to the inorganic particles (A1) before being surface-treated is normally between 0.005 and 0.15, and is preferably between 0.01 and 0.13.

The refractive index of the inorganic particles (A1) is normally 1.52 to 1.58, and is preferably 1.53 to 1.58.

The difference between the refractive index of a polymer of the polymerizable monomers and the refractive index of the inorganic particles (A1) is normally 0.03 or less.

A material constituting the inorganic particles (A1) before being surface-treated is not limited in particular, and may be various kinds of glass that contain silica as a principal component and contain, on an as-needed basis, an oxide of a heavy metal, boron, aluminum or the like (such as E glass, barium glass, and lanthanum glass-ceramics), various kinds of ceramics, a composite oxide (such as silica-titania composite oxide and silica-zirconia composite oxide), kaolin, clay minerals (such as montmorillonite), mica, ytterbium fluoride, yttrium fluoride, or the like, and two or more kinds of these may be used in combination as the material constituting the inorganic particles (A1) before being surface-treated.

A commercially available product of the inorganic particles (A1) may be G018-053, GM27884, 8235, GM31684 (which are manufactured by Schott AG), E2000, E3000 (which are manufactured by ESSTECH, Inc.), or the like.

With the exception of being surface-treated with a compound expressed by the general formula (2), the inorganic particles (A2) are similar to the inorganic particles (A1).

A compound expressed by the general formula (2) is similar to a compound expressed by the general formula (1) except that q is an integer greater than or equal to 1 and less than or equal to 5.

It is more preferable that q in the general formula (2) is an integer greater than or equal to 1 and less than or equal to 3.

The compound expressed by the general formula (2) is not limited in particular, and may be 3-methacryloyloxypropyltrimethoxysilane, 3-acryloyloxypropyltrimethoxysilane, 3-methacryloyloxypropyltriethoxysilane, 3-methacryloyloxypropyldimethoxysilane, 4-methacryloyloxybutyltrimethoxysilane, or the like, and two or more kinds of these may be used in combination as the compound expressed by the general formula (2). Among these, 3-methacryloyloxypropyltrimethoxysilane is preferable.

The inorganic particles (B) may be either spherical or irregularly shaped. Also, the inorganic particles (B) may be either primary particles that are not aggregated or secondary particles into which primary particles aggregate.

Note that in a case in which the inorganic particles (B) are irregularly shaped, the primary particle size is the average value of the long diameters and the short diameters of the inorganic particles (B).

A method of surface-treating the inorganic particles (B) is not limited in particular, and may be a method by which the inorganic particles (B) before being surface-treated are sprayed with a solution obtained by diluting a silane coupling agent or a compound expressed by the general formula (3) with a solvent while being stirred in a mixing tank and are heated and dried for a certain time in the tank while being kept stirred, a method by which the inorganic particles (B) before being surface-treated and a silane coupling agent or a compound expressed by the general formula (3) are stirred and mixed in a solvent and are thereafter heated to be dried, or the like.

A silane coupling agent is not limited in particular as long as it can introduce a group expressed by the chemical formula (A) and/or a group expressed by the chemical formula (B) onto a surface, and may be dimethyldichlorosilane, hexamethyldisilazane, or the like, and two or more kinds of these may be used in combination as the silane coupling agent.

A compound expressed by the general formula (3) is similar to a compound expressed by the general formula (1) except that q is an integer greater than or equal to 1 and less than or equal to 6.

It is more preferable that q in the general formula (3) is an integer greater than or equal to 1 and less than or equal to 3.

The compound expressed by the general formula (3) is not limited in particular, and may be 3-methacryloyloxypropyltrimethoxysilane, 3-acryloyloxypropyltrimethoxysilane, 3-methacryloyloxypropyltriethoxysilane, 3-methacryloyloxypropyldimethoxysilane, 4-methacryloyloxybutyltrimethoxysilane, or the like, and two or more kinds of these may be used in combination as the compound expressed by the general formula (3). Among these, 3-methacryloyloxypropyltrimethoxysilane is preferable.

A material constituting the inorganic particles (B) before being surface-treated is not limited in particular, and may be an inorganic oxide such as silica, alumina, titania, or zirconia, a composite oxide thereof, calcium phosphate, hydroxylapatite, yttrium fluoride, ytterbium fluoride, barium titanate, potassium titanate, or the like. Among these, silica, alumina, titania, silica-alumina composite oxide, and silica-zirconia composite oxide are preferable.

A commercially available product of the inorganic particles (B) before being surface-treated may be Aerosil 200, OX-50 (which are manufactured by Nippon Aerosil Co., Ltd.), or the like.

A commercially available product of the inorganic particles (B) may be Aerosil R812, R972, RX-50 (which are manufactured by Nippon Aerosil Co., Ltd.), or the like.

The refractive index of the inorganic particles (B) is normally 1.43 to 1.50, and is preferably 1.43 to 1.46.

The difference between the refractive index of a polymer of the polymerizable monomers and the refractive index of the inorganic particles (B) is normally 0.05 or more.

The dental curable composition may further include a polymerization initiator.

In a case of curing the dental curable composition according to the present embodiment at room temperature, a redox polymerization initiator can be used.

A redox polymerization initiator is not limited in particular, and may be an organic peroxide/amine system, an organic peroxide/amine/sulfinic acid (or a salt thereof) system, or the like.

Note that in a case of using a redox polymerization initiator, an oxidant and a reductant need to be in a configuration of being separately packaged and be mixed up immediately before use.

An oxidant is not limited in particular, and may be an organic peroxide such as diacyl peroxides, peroxyesters, peroxycarbonates, dialkyl peroxides, peroxyketals, ketone peroxides, or hydroperoxides.

Examples of diacyl peroxides include benzoyl peroxide, 2,4-dichlorobenzoyl peroxide, m-toluoyl peroxide, lauroyl peroxide, and the like.

Examples of peroxyesters include t-butyl peroxybenzoate, di-t-butyl peroxyisophthalate, t-butyl peroxy-2-ethylhexanoate, and the like.

Examples of peroxycarbonates include t-butyl peroxy isopropyl carbonate and the like.

Examples of dialkyl peroxides include dicumyl peroxide, di-t-butyl peroxide, 2,5-dimethyl-2,5-bis(benzoylperoxy)hexane, and the like.

Examples of peroxyketals include 1,1-bis(t-butylperoxy)-3,3,5-trimethylcyclohexane and the like.

Examples of ketone peroxides include methyl ethyl ketone peroxide and the like.

Examples of hydroperoxides include t-butyl hydroperoxide and the like.

Examples of a reductant are not limited in particular, and include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, ethyl 4-dimethylaminobenzoate, n-butoxyethyl 4-dimethylaminobenzoate, 2-methacryloyloxyethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, and the like.

As a redox polymerization initiator other than those described above, an oxidation-reduction initiator such as a cumenehydroperxide/thiourea system, an ascorbic acid/$Cu^{2+}$ salt system, or an organic sulfinic acid (or salt thereof)/amine/inorganic peroxide system, tributylborane, organic sulfinic acid, etc., may also be used.

In a case of irradiating the dental curable composition according to the present embodiment with visible rays to cure the composition, a photopolymerization initiator can be used.

A photopolymerization initiator is not limited in particular, and may be an oxidation-reduction initiator such as α-diketone/reductant, ketal/reductant, thioxanthone/reductant, or the like Examples of α-diketone includes camphorquinone, benzyl, 2,3-pentanedione, and the like.

Examples of ketal include benzyl dimethyl ketal, benzyl diethyl ketal, and the like.

Examples of thioxanthone include 2-chlorothioxanthone, 2,4-diethylthioxantone, and the like.

Examples of a reductant include tertiary amines such as Michler's ketone, 2-(dimethylamino)ethyl methacrylate, N,N-bis[(meth)acryloyloxyethyl]-N-methylamine, ethyl N,N-dimethylaminobenzoate, butyl 4-dimethylaminobenzoate, butoxyethyl 4-dimethylaminobenzoate, N-methyldiethanolamine, 4-dimethylaminobenzophenone, N,N-bis(2-hydroxyethyl)-p-toluidine, and dimethylaminophenanthrol; aldehydes such as citronellal, lauryl aldehyde, phthaldialdehyde, dimethylaminobenzaldehyde, and terephthalaldehyde; and compounds having a thiol group, such as 2-mercaptobenzoxazole, decanethiol, 3-mercaptopropyltrimethoxysilane, 4-mercaptoacetophenone, thiosalicylic acid, and thiobenzoic acid.

Note that an organic peroxide may be added to an oxidation-reduction initiator.

In a case of irradiating the dental curable composition according to the present embodiment with ultraviolet rays to cure the composition, a photopolymerization initiator can be used.

A photopolymerization initiator is not limited in particular, and may be a benzoin alkyl ether, a benzyl dimethyl ketal, an acylphosphine oxide, an bisacylphosphine oxide, or the like.

Examples of an acylphosphine oxide include 2,4,6-trimethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl bis(2,6-dimethylphenyl)phosphonate, 2,4,6-trimethylbenzoylethoxyphenylphosphine oxide, and the like.

Examples of a bisacylphosphine oxide include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and the like.

Note that a (bis)acylphosphine oxide may be substituted by a water-soluble substituent.

Also, a (bis)acylphosphine oxide may be used in combination with a reductant such as amines, aldehydes, mercaptans, or sulfinic acid salts.

The mass ratio of the polymerization initiator to the polymerizable monomers is normally between 0.001 and 0.1, and is preferably between 0.002 and 0.05.

The dental curable composition according to the present embodiment may further include a polymerization inhibitor, an ultraviolet absorber, a fluorescent agent, a pigment, and the like.

A polymerization inhibitor is not limited in particular, and may be 3,5-dibutyl-4-hydroxytoluene, hydroquinone, dibutylhydroquinone, dibutylhydroquinone monomethyl ether, 2,6-t-butylphenol, 4-methoxyphenol, or the like, and two or more kinds of these may be used in combination as the polymerization inhibitor.

Note that the dental curable composition may be used as a paste in which the inorganic particles (A1) and/or the inorganic particles (A2); and the inorganic particles (B) are dispersed in the polymerizable monomers or may be used a molded body in which the polymerizable monomers; the inorganic particles (A1) and/or the inorganic particles (A2); and the inorganic particles (B) are dispersed in the cured polymerizable monomers.

For example, a cavity in an oral cavity can be directly filled with a paste in which the inorganic particles (A1) and/or the inorganic particles (A2); and the inorganic particles (B) are dispersed in the polymerizable monomers. Also, after curing and molding the paste, in which the inorganic particles (A1) and/or the inorganic particles (A2); and the inorganic particles (B) are dispersed in the polymerizable monomers, outside the oral cavity, the molded body can be attached inside the oral cavity using a dental adhesive.

Here, when the dental curable composition is chemically polymerizable (and photopolymerizable), a composition containing an oxidant and a composition containing a reductant need to be in a configuration of being separately packaged and be mixed up immediately before use of the dental curable composition.

The dental curable composition according to the present embodiment is preferably a flowable composite resin. At this point, the flowable composite resin may be either of an one-agent type or of a two-agent type.

The extrusion strength of the flowable composite resin is normally 10 kgf or less. This makes it possible to enhance the formability and handleability of the flowable composite resin.

The flowable composite resin is provided, for example, as a package that includes a syringe filled with the flowable composite resin, a plunger fitted into the syringe from the rear end side of the syringe, and a needle chip that is attached to the tip portion of the syringe.

The inner diameter of the needle that the needle chip includes normally 0.3 to 0.9 mm.

When the flowable composite resin is of a two-agent type, the package may include, for example, two syringes connected in parallel and two plungers connected in parallel, and a static mixer may be provided at the tip portion of each of the syringes.

EXAMPLES

The present invention is described in detail below with reference to Examples and Comparative Examples, but is not limited to the Examples. Note that part means part by mass.

[Manufacture of Inorganic Particles (A1-1)]

Irregularly-shaped barium glass particles GM27884 NanoFine 180 (manufactured by Schott AG) having a volume-median particle size of 0.18 μm were surface-treated with 8-methacryloyloxyoctyltrimethoxysilane to obtain inorganic particles (A-1) having a volume-median particle size of 0.18 μm.

[Manufacture of Inorganic Particles (A1-2)]

Inorganic particles (A1-2) having a volume-median particle size of 0.4 μm were obtained in the same manner as the inorganic particles (A1-1) except for using barium glass particles GM27884 Ultra Fine 0.4 (manufactured by Schott AG) having a volume-median particle size of 0.40 μm instead of irregularly-shaped barium glass particles GM27884 NanoFine 180 (manufactured by Schott AG) having a volume-median particle size of 0.18 μm.

[Manufacture of Inorganic Particles (A1-3)]

Inorganic particles (A1-3) having a volume-median particle size of 0.7 μm were obtained in the same manner as the inorganic particles (A1-1) except for using barium glass particles GM27884 Ultra Fine 2.0 (manufactured by Schott AG) having a volume-median particle size of 0.70 μm instead of irregularly-shaped barium glass particles GM27884 NanoFine 180 (manufactured by Schott AG) having a volume-median particle size of 0.18 μm.

[Manufacture of Inorganic Particles (A1-4)]

Inorganic particles (A1-4) having a volume-median particle size of 1.0 μm were obtained in the same manner as the inorganic particles (A1-1) except for using barium glass particles GM27884 Ultra Fine 2.0 (manufactured by Schott AG) having a volume-median particle size of 1.0 μm instead of irregularly-shaped barium glass particles GM27884 NanoFine 180 (manufactured by Schott AG) having a volume-median particle size of 0.18 μm.

[Manufacture of Inorganic Particles (A2-1)]

Inorganic particles (A2-1) having a volume-median particle size of 0.18 μm were obtained in the same manner as the inorganic particles (A1-1) except for using 3-methacryloyloxypropyltrimethoxysilane instead of 8-methacryloyloxyoctyltrimethoxysilane.

[Manufacture of Inorganic Particles (A2-2)]

Inorganic particles (A2-2) having a volume-median particle size of 0.4 μm were obtained in the same manner as the inorganic particles (A1-2) except for using 3-methacryloyloxypropyltrimethoxysilane instead of 8-methacryloyloxyoctyltrimethoxysilane.

[Manufacture of Inorganic Particles (A2-3)]

Inorganic particles (A2-3) having a volume-median particle size of 0.7 μm were obtained in the same manner as the inorganic particles (A1-3) except for using 3-methacryloyloxypropyltrimethoxysilane instead of 8-methacryloyloxyoctyltrimethoxysilane.

Table 1 illustrates characteristics of the inorganic particles (A1) and (A2).

TABLE 1

| INORGANIC PARTICLES | VOLUME-MEDIAN PARTICLE SIZE [μm] | SURFACE TREATMENT AGENT |
|---|---|---|
| A1-1 | 0.18 | 8-METHACRYLOYLOXYOCTYLTRIMETHOXYSILANE |
| A1-2 | 0.40 | 8-METHACRYLOYLOXYOCTYLTRIMETHOXYSILANE |
| A1-3 | 0.70 | 8-METHACRYLOYLOXYOCTYLTRIMETHOXYSILANE |
| A1-4 | 1.0 | 8-METHACRYLOYLOXYOCTYLTRIMETHOXYSILANE |
| A2-1 | 0.18 | 3-METHACRYLOYLOXYPROPYLTRIMETHOXYSILANE |
| A2-2 | 0.40 | 3-METHACRYLOYLOXYPROPYLTRIMETHOXYSILANE |
| A2-3 | 0.70 | 3-METHACRYLOYLOXYPROPYLTRIMETHOXYSILANE |

[Volume-Median Particle Size of Inorganic Particles (A1) and (A2)]

After 15 mg of the inorganic particles (A1) or the inorganic particles (A2) were added to 20 mL of a 0.2 mass % sodium hexametaphosphate solution, the inorganic particles (A1) or the inorganic particles (A2) were dispersed for 30 minutes using an ultrasonic disperser to obtain a dispersion of the inorganic particles (A1) or the inorganic particles (A2). Then, the volume-median particle size of the inorganic particles (A1) or the inorganic particles (A2) was measured using a laser diffraction particle size distribution analyzer LA-950 (manufactured by HORIBA, Ltd).

[Inorganic Particles (B-1)]

Silica particles Aerosil R812 (manufactured by Nippon Aerosil Co., Ltd.), having an average primary particle size of 7 nm and surface-treated with hexamethyldisilazane, were used as inorganic particles (B-1).

[Inorganic Particles (B-2)]

Silica particles Aerosil R972 (manufactured by Nippon Aerosil Co., Ltd.), having an average primary particle size of 16 nm and surface-treated with dimethyldichlorosilane, were used as inorganic particles (B-2).

[Inorganic Particles (B-3)]

Silica particles Aerosil OX-50 (manufactured by Nippon Aerosil Co., Ltd.) having an average primary particle size of 40 nm were treated with 3-methacryloyloxypropyltrimethoxysilane to obtain inorganic particles (B-3) having an average primary particle size of 40 nm.

Table 2 indicates characteristics of the inorganic particles (B).

[Average Primary Particle Size of Inorganic Particles (B)]

Electron micrographs of 100 inorganic particles (B) were subjected to image analysis using image analysis software WinROOF (manufactured by MITANI Corporation), and thereafter, the average primary particle size of the inorganic particles (B) was calculated as a volume average particle size.

[Preparation of Polymerizable Composition]

30 parts of di-2-methacryloyloxyethyl-2,2,4-trimethylhexamethylene dicarbamate (UDMA), 50 parts of 2,2-bis[4-(2-methacryloyloxyethoxy)phenyl]propane (Bis-MEPP), 10 parts of triethylene glycol dimethacrylate (3G), and 10 parts of trimethylolpropane trimethacrylate (TMPT) were mixed to obtain a mixture of polymerizable monomers.

To the mixture of polymerizable monomers, 1 parts of camphorquinone (CQ), 2 parts of ethyl 4-dimethylaminobenzoate, 0.2 parts of diethyl-2,5-dihydroxy terephthalate (LZ), and 0.2 parts of 2,5-bis (5'-t-butylbenzoxazolyl-2') thiophene (TF) were added to obtain a polymerizable composition.

Example 1

To 50.0 parts of the polymerizable composition, 99.9 parts of the inorganic particles (A1-1) and 0.1 parts of the inorganic particles (B-1) were added to be homogeneously mixed and kneaded. Thereafter, vacuum defoaming was performed to obtain a flowable composite resin in a paste state.

Example 2

With the exception of changing the 99.9 parts of the inorganic particles (A1-1) to 70.0 parts of the inorganic particles (A1-1) and 29.9 parts of the inorganic particles (A1-2), a flowable composite resin in a paste state was obtained similarly to Example 1.

Example 3

To 50.0 parts of the polymerizable composition, 30.0 parts of the inorganic particles (A1-1), 30.0 parts of the inorganic

TABLE 2

| INORGANIC PARTICLES | AVERAGE PRIMARY PARTICLE SIZE [nm] | SURFACE TREATMENT AGENT |
|---|---|---|
| B-1 | 7 | HEXAMETHYLDISILAZANE |
| B-2 | 16 | DIMETHYLDICHLOROSILANE |
| B-3 | 40 | 3-METHACRYLOYLOXYPROPYLTRIMETHOXYSILANE | particles (A1-2), 38.5 parts of the inorganic particles (A1-3), and 1.5 parts of the inorganic particles (B-2) were added to be homogeneously mixed and kneaded. Thereafter, vacuum defoaming was performed to obtain a flowable composite resin in a paste state.

Example 4

To 50.0 parts of the polymerizable composition, 20.0 parts of the inorganic particles (A1-1), 79.5 parts of the inorganic particles (A2-2), and 0.5 parts of the inorganic particles (B-3) were added to be homogeneously mixed and kneaded. Thereafter, vacuum defoaming was performed to obtain a flowable composite resin in a paste state.

Example 5

To 50.0 parts of the polymerizable composition, 15.0 parts of the inorganic particles (A1-1), 20.0 parts of the inorganic particles (A1-2), 20.0 parts of the inorganic particles (A1-3), 10.0 parts of the inorganic particles (A1-1), 14.0 parts of the inorganic particles (A2-2), 20.0 parts of the inorganic particles (A2-3), 0.5 parts of the inorganic particles (B-1), and 0.5 parts of the inorganic particles (B-2) were added to be homogeneously mixed and kneaded. Thereafter, vacuum defoaming was performed to obtain a flowable composite resin in a paste state.

Example 6

To 50.0 parts of the polymerizable composition, 59.0 parts of the inorganic particles (A1-2), 40.0 parts of the inorganic particles (A2-2), and 1.0 parts of the inorganic particles (B-3) were added to be homogeneously mixed and kneaded. Thereafter, vacuum defoaming was performed to obtain a flowable composite resin in a paste state.

Example 7

To 50.0 parts of the polymerizable composition, 98.5 parts of the inorganic particles (A1-3) and 1.5 parts of the inorganic particles (B-3) were added to be homogeneously mixed and kneaded. Thereafter, vacuum defoaming was performed to obtain a flowable composite resin in a paste state.

Comparative Example 1

To 50.0 parts of the polymerizable composition, 100.0 parts of the inorganic particles (A1-2) were added to be homogeneously mixed and kneaded. Thereafter, vacuum defoaming was performed to obtain a flowable composite resin in a paste state.

Comparative Example 2

To 50.0 parts of the polymerizable composition, 99.0 parts of the inorganic particles (A1-4) and 1.0 parts of the inorganic particles (B-1) were added to be homogeneously mixed and kneaded. Thereafter, vacuum defoaming was performed to obtain a flowable composite resin in a paste state.

Comparative Example 3

To 50.0 parts of the polymerizable composition, 80.0 parts of the inorganic particles (A1-1), 18.0 parts of the inorganic particles (A2-1), and 2.0 parts of the inorganic particles (B-1) were added to be homogeneously mixed and kneaded. Thereafter, vacuum defoaming was performed to obtain a flowable composite resin in a paste state.

Table 3 indicates characteristics of the flowable composite resins of Examples and Comparative Examples.

TABLE 3

| | INORGANIC PARTICLES A1 | | INORGANIC PARTICLES A2 | | INORGANIC PARTICLES B | | EXTRUSION STRENGTH [kgf] |
|---|---|---|---|---|---|---|---|
| | TYPE | ADDITIVE AMOUNT [PART] | TYPE | ADDITIVE AMOUNT [PART] | TYPE | ADDITIVE AMOUNT [PART] | |
| E1 | A1-1 | 99.9 | — | — | B-1 | 0.1 | 6 |
| E2 | A1-1 A1-2 | 99.9 | — | — | B-1 | 0.1 | 5 |
| E3 | A1-1 A1-2 A1-3 | 98.5 | — | — | B-2 | 1.5 | 3 |
| E4 | A1-1 | 20.0 | A2-2 | 79.5 | B-3 | 0.5 | 8 |
| E5 | A1-1 A1-2 A1-3 | 55.0 | A2-1 A2-2 A2-3 | 44.0 | B-1 B-2 | 1.0 | 4 |
| E6 | A1-2 | 59.0 | A2-2 | 40.0 | B-3 | 1.0 | 6 |
| E7 | A1-3 | 98.5 | — | — | B-3 | 1.5 | 2 |
| CE1 | A1-2 | 100.0 | — | — | — | — | 6 |
| CE2 | A1-4 | 99.0 | — | — | B-1 | 1.0 | 2 |
| CE3 | A1-1 | 80.0 | A2-1 | 18.0 | B-1 | 2.0 | 10 |

[Extrusion Strength]

Extrusion strength was evaluated using a cylindrical polyolefin resin syringe (an MI filling container of 7.7 mm in inner diameter and 78.6 mm in length), a cylindrical plunger fitted into the syringe from the rear end side of the syringe, and a needle chip (20G) that is attached to the tip portion of the syringe. Here, the needle of the needle chip is 0.65 mm in inner diameter and 13 mm in length, and is bent 50° at a position 7.5 mm from the tip. Also, the syringe and the plunger are formed of a member opaque to environmental light.

First, after filling the syringe with 2.0 mL of a flowable composite resin, the needle chip was attached to the tip portion of the syringe, and the plunger was pushed to extrude the flowable composite resin from the tip of the needle chip. At this point, extrusion strength was measured at 25° C., using a universal testing machine AG-IS (manufactured by Shimadzu Corporation). Specifically, while vertically retaining the storage container, a crosshead to which a jig for compressive strength test was attached was lowered at 10 mm/min to apply a load on and extrude the flowable composite resin, and a maximum load at the time was determined as extrusion strength.

Then, the stringiness, the flexural strength, the abrasion resistance, the polishability, the formability, the handleability, and the liquid separation of the flowable composite resins were evaluated.

[Stringiness]

A ring made of acrylic resin having an inner diameter of 10 mm and a thickness of 2 mm was filled with a flowable composite resin, and a cylindrical rod made of plastic having a diameter of 5 mm was immersed in the central portion of the ring by 1 mm. Using a universal testing machine AG-IS (manufactured by Shimadzu Corporation), the cylindrical rod was pulled up at a speed of 50 mm/min, and the distance at which the paste was cut off was measured to determine the stringiness length. Note that a stringiness length of 30 mm or less was determined as being acceptable.

[Flexural Strength]

After filling a stainless steel mold of 2 mm×2 mm×25 mm with a flowable composite resin, the upper side and the lower side of the flowable composite resin were pressed with slide glasses. Next, the flowable composite resin was cured by irradiating the upper surface and the lower surface at nine points on each surface with visible light for 10 seconds per point, using a G-Light Prima-II (manufactured by GC Corporation). Then, after being extracted from the mold, the cured product was stored in distilled water at 37° C. for 24 hours to obtain a test piece. At this point, five test pieces were made.

Next, the flexural strength of the five test pieces was measured using a universal testing machine AG-IS (manufactured by Shimadzu Corporation) with the distance between support points being 20 mm and the crosshead speed being 1 mm/min, and thereafter, the average value was calculated to be determined as flexural strength. Note that a flexural strength of 160 MPa or more was determined as being acceptable.

[Abrasion Resistance]

After filling a dedicated mold with a flowable composite resin, the upper side and the lower side of the flowable composite resin were pressed with slide glasses. Next, the upper surface and the lower surface of the flowable composite resin were irradiated with visible light for 10 seconds using a G-Light Prima-II (manufactured by GC Corporation) to cure the flowable composite resin. Furthermore, after being extracted from the mold, the cured product was stored in distilled water at 37° C. for 24 hours to obtain a test piece.

Each test piece was attached to a bite abrasion tester (manufactured by TOKYO GIKEN, INC.), and after polishing an unpolymerized layer with #1000 abrasive paper, the overall length of the test piece before testing was measured. A slurry obtained by mixing and kneading the equal amounts of glycerin and Acricone AC (manufactured by Mitsubishi Rayon Co., Ltd.) was laid on the bite abrasion tester, and a test assuming 100,000 vertical and lateral bites was conducted against a PMMA plate. After the test, the overall length of each test piece was measured. The abrasion resistance was evaluated by determining the difference between before and after the test as the amount of wear. Note that a wear of 10 μm or less was determined as being acceptable

[Polishability]

After filling a mold of 15 mm in diameter and 1.5 mm in thickness with a flowable composite resin, the upper side and the lower side of the flowable composite resin were pressed with slide glasses. Next, the flowable composite resin was cured by irradiating the upper surface and the lower surface at nine points on each surface with visible light for 10 seconds per point, using a G-Light Prima-II (manufactured by GC Corporation). Furthermore, the cured product was extracted from the mold to obtain a test piece. Next, a smooth surface of the test piece was polished under a dry condition, using #600 abrasive paper. Furthermore, using MICROMOTOR LM-III (manufactured by GC Corporation), with water being injected, polishing was performed for 10 seconds at a rotational speed of approximately 10,000 rpm using PRE SHINE (manufactured by GC Corporation), and thereafter, polishing was performed for 10 seconds at a rotational speed of approximately 10,000 rpm using DIA SHINE (manufactured by GC Corporation). Next, the glossiness of the polished surface was measured at a measurement angle of 60°, using a glossmeter VG-2000 (manufactured by NIPPON DENSHOKU INDUSTRIES CO., LTD.), and its ratio to that of a mirror serving as 100 was determined as glossiness to evaluate the polishability. Note that a glossiness of 60% or more was determined as being acceptable.

[Formability and Handleability]

Using the above-described syringe, plunger, and needle chip, 0.03 g of a flowable composite resin were extruded onto white mixing paper to evaluate the formability and handleability. Note that the formability and handleability were determined based on the following criteria.

A: The viscosity of a flowable composite resin is appropriate to make it possible to very easily build up and correct the shape of the flowable composite resin.

B: The viscosity of a flowable composite resin is appropriate to make it possible to easily build up and correct the shape of the flowable composite resin.

C: The viscosity of a flowable composite resin is high to make it impossible to correct the shape of the flowable composite resin, or the viscosity of a flowable composite resin is low to make it impossible to build up the flowable composite resin.

[Liquid Separation]

First, the above-described syringe was filled with 2.0 mL of a flowable composite resin, and then centrifuged at 760 g for 2 hours. Next, 0.5 g of the flowable composite resin was extracted from each of the tip and the rear end of the syringe into a crucible, and then burned at 700° C. At this time, the weight after burning was measured to calculate the difference between the contents of the inorganic particles at the tip and the rear end of the syringe, and the liquid separation was evaluated. Note that the liquid separation was determined based on the following criteria.

A: The difference between the contents of the inorganic particles at the tip and the rear end of the syringe is less than 1% by weight.

B: The difference between the contents of the inorganic particles at the tip and the rear end of the syringe is greater than or equal to 1% by weight.

Table 4 indicates the evaluation results of the stringiness, the flexural strength, the abrasion resistance, the polishability, the formability, the handleability, and the liquid separation of the flowable composite resins.

TABLE 4

| | STRINGINESS LENGTH [mm] | FLEXURAL STRENGTH [MPa] | AMOUNT OF WEAR [μm] | GLOSSINESS [%] | FORMABILITY AND HANDLEABILITY | LIQUID SEPARATION |
|---|---|---|---|---|---|---|
| E1 | 20 | 161 | 3 | 73 | B | A |
| E2 | 22 | 168 | 3 | 70 | B | A |
| E3 | 26 | 162 | 7 | 64 | B | A |
| E4 | 22 | 174 | 4 | 67 | A | A |
| E5 | 23 | 169 | 7 | 63 | A | A |
| E6 | 23 | 163 | 5 | 65 | A | A |
| E7 | 26 | 163 | 9 | 61 | B | A |
| CE1 | 21 | 167 | 5 | 65 | B | B |
| CE2 | 21 | 138 | 32 | 32 | B | A |
| CE3 | 51 | 162 | 3 | 72 | B | A |

It is apparent from Table 4 that the flowable composite resins of Examples 1 to 7 reduce the stringiness, suppress the liquid separation, and are excellent in the flexural strength, the abrasion resistance, the polishability, the formability, and the handleability.

In contrast, because the flowable composite resin of Comparative Example 1 does not contain inorganic particles (B), liquid separation easily occurs.

Because the flowable composite resin of Comparative Example 2 contains inorganic particles (A1-4) having a volume-median particle size of 1.0 μm, the flexural strength, the abrasion resistance, and the polishability are low.

In the flowable composite resin of Comparative Example 3, because the ratio of the mass of the inorganic particles (B-1) to the total mass of the inorganic particles (A1-1), the inorganic particles (A 2-1), and the inorganic particles (B-1) is 0.02, the stringiness is large.

The present international application is based upon and claims the benefit of priority of Japanese Patent Application No. 2017-035297, filed on Feb. 27, 2017, the entire contents of Japanese Patent Application No. 2017-035297 are hereby incorporated herein by reference.

The invention claimed is:

1. A dental curable composition comprising:
polymerizable monomers;
inorganic particles (A1) or the inorganic particles (A1) and inorganic parties (A2); and
inorganic particles (B),
wherein the inorganic particles (A1) are surface-treated with a compound expressed by a general formula

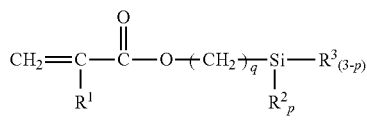
(1)

(in the formula, $R^1$ is a hydrogen atom or a methyl group, $R^2$ is a hydrolyzable group, $R^3$ is a hydrocarbon group having 1 to 6 carbon atoms, p is 2 or 3, and q is an integer greater than or equal to 1 and less than or equal to 13), and the inorganic particles (A1) have a volume-median particle size of greater than or equal to 0.1 μm and less than or equal to 0.9 μm,
wherein the inorganic particles (A2) are surface-treated with a compound expressed by a general formula

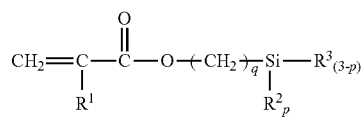
(2)

(in the formula, $R^1$ is a hydrogen atom or a methyl group, $R^2$ is a hydrolyzable group, $R^3$ is a hydrocarbon group having 1 to 6 carbon atoms, p is 2 or 3, and q is an integer greater than or equal to 1 and less than or equal to 5), and the inorganic particles (A2) have a volume-median particle size of greater than or equal to 0.1 μm and less than or equal to 0.9 μm,
wherein the inorganic particles (B) are particles where a group expressed by a following general formula

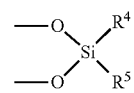
(A)

(in the formula, $R^4$ and $R^5$ are independently a methyl group or an ethyl group) is present at surfaces, are particles where a group expressed by a following general formula

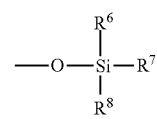
(B)

(in the formula $R^6$, $R^7$, and $R^8$ are independently a methyl group or an ethyl group) is present at surfaces, and/or are particles surface-treated with a compound expressed by a general formula

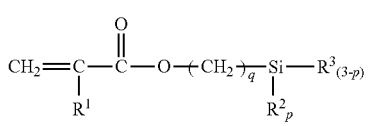
(3)

(in the formula $R^1$ is a hydrogen atom or a methyl group, $R^2$ is a hydrolyzable group, $R^3$ is a hydrocarbon group having 1 to 6 carbon atoms, p is 2 or 3, and q is an integer greater than or equal to 1 and less than or equal to 6), and the inorganic particles (B) have an average primary particle size of greater than or equal to 5 nm and less than or equal to 50 nm, and wherein a ratio of a mass of the inorganic particles (B) to a total mass of the inorganic particles (A1), the inorganic particles (A2), and the inorganic particles (B) is greater than or equal to 0.001 and less than or equal to 0.015.

2. The dental curable composition as claimed in claim 1, wherein a ratio of a mass of the inorganic particles (A1) to the total mass of the inorganic particles (A1), the inorganic particles (A2), and the inorganic particles (B) is greater than or equal to 0.2.

3. The dental curable composition as claimed in claim 1, wherein the dental curable composition is a flowable composite resin.

* * * * *